(12) United States Patent
Dong et al.

(10) Patent No.: US 10,548,559 B2
(45) Date of Patent: Feb. 4, 2020

(54) METHOD FOR CALIBRATING WORKING PLANE OF MEDICAL DETECTION APPARATUS

(71) Applicant: General Electric Company, Schenectady, NY (US)

(72) Inventors: Yifei Dong, Beijing (CN); Kai Wang, Beijing (CN)

(73) Assignee: General Electric Company, Schenectady, NY (US)

( * ) Notice: Subject to any disclaimer, the term of this patent is extended or adjusted under 35 U.S.C. 154(b) by 322 days.

(21) Appl. No.: 15/612,607

(22) Filed: Jun. 2, 2017

(65) Prior Publication Data

US 2017/0360393 A1      Dec. 21, 2017

(30) Foreign Application Priority Data

Jun. 15, 2016      (CN) .......................... 2016 1 0417301

(51) Int. Cl.
*A61B 6/00* (2006.01)
*A61B 6/02* (2006.01)
*A61B 6/03* (2006.01)

(52) U.S. Cl.
CPC ................ *A61B 6/585* (2013.01); *A61B 6/58* (2013.01); *A61B 6/582* (2013.01); *A61B 6/583* (2013.01); *A61B 6/02* (2013.01); *A61B 6/032* (2013.01)

(58) Field of Classification Search
CPC .... A61B 6/00; A61B 6/02; A61B 6/03; A61B 6/585; A61B 6/583; A61B 6/58; A61B 6/032; A61B 6/582; A61B 6/04; A61B 6/0407; A61N 5/1075
See application file for complete search history.

*Primary Examiner* — Jurie Yun

(57) ABSTRACT

A method for calibrating a working plane of a medical detection apparatus in parallel with a first reference plane is provided. The working plane has first and second points to be calibrated thereon. The first and second points are supporting points of first and second foots of the working plane respectively. The method includes receiving a first inclination angle value which is an angle between a line connecting the first and second points and the first reference plane; computing a vertical distance between the second point to be calibrated and the first reference plane as a first magnitude of adjustment according to a pre-stored distance between the first and second points and the first inclination angle value; and adjusting a height of the second foot according to the first magnitude of adjustment to allow the second point to be located on the first reference plane.

9 Claims, 3 Drawing Sheets

1

METHOD FOR CALIBRATING WORKING PLANE OF MEDICAL DETECTION APPARATUS

FIELD

The present invention relates to the field of medical detection, particularly to a method for calibrating a working plane of a medical detection apparatus.

BACKGROUND OF THE INVENTION

A medical detection apparatus is, e.g., a computed tomography imaging apparatus, a magnetic resonance imaging apparatus, an X-ray machine, etc., and in order to ensure its imaging quality, a higher requirement is also needed for accuracy of a mechanical component such as a detection bed, a gantry and the like thereon. Take a detection bed of a computed tomography imaging apparatus as an example, it is generally required that a working plane of the detection bed can be kept to be parallel with a horizontal plane; however, during use of the computed tomography imaging apparatus, a field engineer is often needed to calibrate the working plane of the detection bed so as to avoid its inclination. Surely, for other mechanical components other than the detection bed, the working planes thereof often need to be calibrated, too.

One of methods for calibrating a working plane of a medical detection apparatus is to adjust a height or altitude of a supporting component (e.g., a foot) that supports the working plane. During the adjustment, the field engineer usually relies on naked eyes to observe a bubble level on the working plane in order to decide whether the working plane is inclined or not. If the working plane is inclined, the engineer is needed to adjust a height of a foot of the working plane by means of experience. Since the working plane generally has a plurality of feet and a deviation often occurs during the adjustment, there is a necessity of repeatedly observing the bubble level and repeatedly adjusting the feet, which needs a relatively long time, and hard to achieve a desired calibration accuracy, resulting in low working efficiency.

Therefore, in order to improve a calibration accuracy of a working plan of a medical detection apparatus and save calibration time, there is a need to provide a novel method for calibrating a working plane of a medical detection apparatus.

SUMMARY OF INVENTION

An exemplary embodiment of the present invention provides a method for calibrating a working plane of a medical detection apparatus, which is used for calibrating the working plane of the medical detection apparatus to be parallel with a first reference plane, wherein the working plane has a first point to be calibrated and a second point to be calibrated thereon, the first point to be calibrated serving as a first reference point and located on the first reference plane, and the first point to be calibrated and the second point to be calibrated are respectively supporting points of a first foot and a second foot on the working plane on the medical detection apparatus, the first foot and the second foot for supporting the working plane, the above method for calibrating a working plane of a medical detection apparatus comprising:

receiving at least one first inclination angle value from an angle measuring tool, wherein each first inclination angle value is an angle between a line connecting the first point to be calibrated and the second point to be calibrated and the first reference plane;

computing a vertical distance between the second point to be calibrated and the first reference plane as a first magnitude of adjustment according to a pre-stored distance between the first point to be calibrated and the second point to be calibrated and the received first inclination angle value; and adjusting a height of the second foot according to the first magnitude of adjustment to allow the second point to be calibrated to be located on the first reference plane.

Other features and aspects will be apparent through the following detailed description, figures and claims.

BRIEF DESCRIPTION OF THE DRAWINGS

The present invention can be understood better in light of the description of exemplary embodiments of the present invention with reference to the accompanying drawings, in which.

DETAILED DESCRIPTION

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
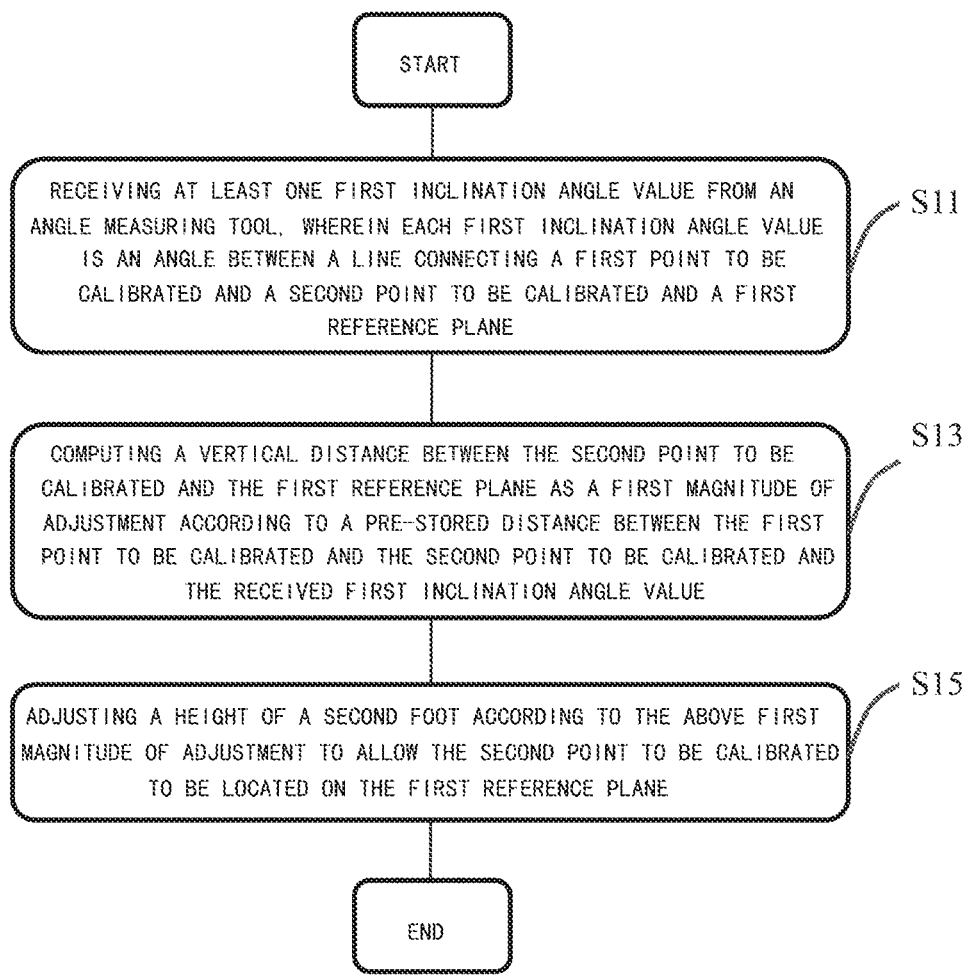
FIG. 1 is a flow chart of a method for calibrating a working plane of a medical detection apparatus provided by one embodiment of the present invention.
Figure 2:
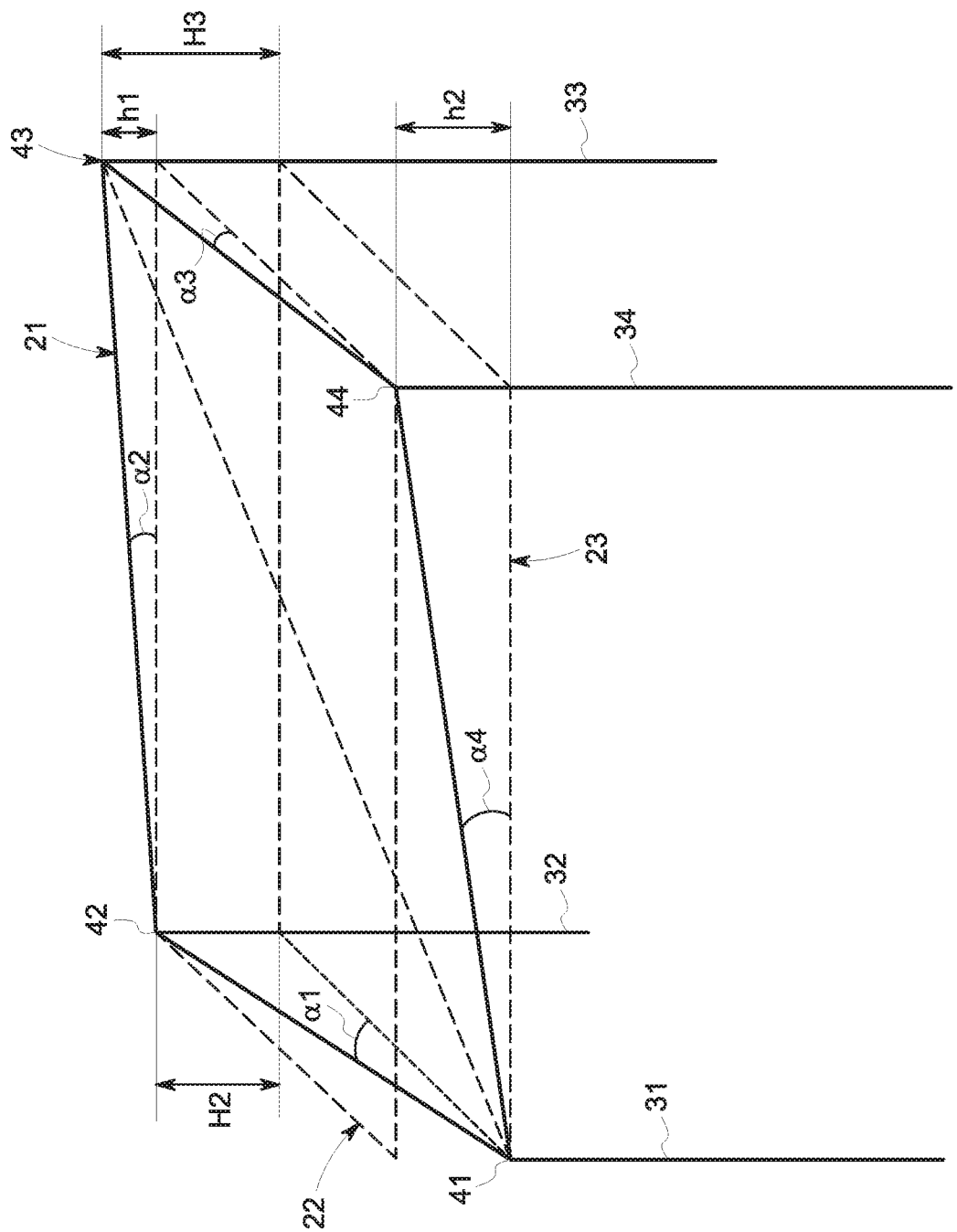
FIG. 2 is an exemplary schematic diagram of the above working plane of the medical detection apparatus.

FIG. 1 is a flow chart of a method for calibrating a working plane of a medical detection apparatus provided by one embodiment of the present invention; and FIG. 2 is one exemplary schematic diagram of the above working plane of the medical detection apparatus. As shown in FIG. 1 and FIG. 2, the method for calibrating a working plane of a medical detection apparatus according to the present invention is used for calibrating a working plane 21 of a medical detection apparatus to be parallel with a first reference plane 23.

The above medical detection apparatus may include a computed tomography imaging apparatus, a magnetic resonance imaging apparatus, or an X-ray machine or the like, and the above working plane may include, e.g., a plane of a detection bed, a plane of a gantry, or a mesa of other mechanical components or the like, and the other mechanical components may be, for example, any components in the medical detection apparatus that can play a supporting role.

As shown in FIG. 2, in an embodiment of the present invention, the above medical detection apparatus may include a plurality of feet, e.g., a first foot 31, a second foot 32, a third foot 33 and a fourth foot 34. The above plurality of feet are used for supporting the working plane 21 and may be located at a plurality of corners of the working plane 21 respectively.

In an embodiment of the present invention, corresponding to the plurality of feet, the above working plane 21 may have a plurality of points to be calibrated thereon, e.g., a first point to be calibrated 41, a second point to be calibrated 42, a third point to be calibrated 43 and a fourth point to be calibrated 44. The above first point to be calibrated 41 to fourth point to be calibrated 44 may be supporting points of the first foot 31 to the fourth foot 34 on the working plane 21 on the medical detection apparatus respectively, the first foot 31 to the fourth foot 34 for supporting the working plane 21.

When the working plane 21 is calibrated, anyone of the points to be calibrated may be used as a reference point such that a plane where said point to be calibrated resides is used as a reference plane, and other points to be calibrated are allowed to also be located on the reference plane by adjusting heights of the corresponding feet. For example, in an embodiment of the present invention, the first point to be calibrated 41 may be used as a first reference point, and thereby a plane where the first point to be calibrated 41 resides may just be used as a first reference plane 23.

As shown in FIG. 1, the method for calibrating a working plane of a medical detection apparatus according to the embodiment of the present invention may include the following steps: an angle value receiving step S11, an amplitude-of-adjustment determining step S13 and an adjusting step S15. The above steps will be described below:

The angle value receiving step S11: receiving at least one first inclination angle value from an angle measuring tool, wherein each first inclination angle value is an angle between a line connecting the first point to be calibrated 41 and the second point to be calibrated 42 and the first reference plane 23; take FIG. 2 as an example for illustrating, if the first point to be calibrated 41 is used as a reference point, the above at least one first inclination angle value may include, e.g., angle values of angles α1 and α4 in FIG. 2, wherein α1 is an angle between a line connecting the first point to be calibrated 41 and the second point to be calibrated 42 and the first reference plane 23, and α4 is an angle between a line connecting the fourth point to be calibrated 44 and the first point to be calibrated 41 and the first reference plane 23.

The amplitude-of-adjustment determining step S13: computing a vertical distance H2 between the second point to be calibrated 42 and the first reference plane as a first magnitude of adjustment according to a pre-stored distance L2 between the first point to be calibrated 41 and the second point to be calibrated 42 and the received first inclination angle value. In one embodiment, the above pre-stored distance L2 between the first point to be calibrated 41 and the second point to be calibrated 42 is just a horizontal distance between the corresponding first foot 31 and second foot 32, and said distance is fixed.

Specifically, in the amplitude-of-adjustment determining step S13, the above first amplitude of adjustment may be computed according to the following Equation (1):

$$H2 = L2 * \tan \alpha 1 \quad (1)$$

Wherein H2 is the first amplitude of adjustment, L2 is the pre-stored distance between the first point to be calibrated 41 and the second point to be calibrated 42, and α1 is the first inclination angle value.

According to the following description, for the fourth point to be calibrated 44, a vertical distance between the fourth point to be calibrated 44 and the first reference plane 23, i.e., a distance between the fourth point to be calibrated 44 and the first point to be calibrated 41 in a vertical direction, may also be computed in the above manner.

For the third point to be calibrated 43, a vertical distance H3 between the third point to be calibrated 43 and the first reference plane 22 may also be computed in the above manner. For example, a line connecting the third point to be calibrated 43 and the first point to be calibrated 41 is just one diagonal on the working plane in FIG. 2, and the above vertical distance H3 may just be obtained by pre-storing a length of the diagonal and measuring an inclination angle of the working plane 23 along a direction of said diagonal.

The adjusting step S15: adjusting a height of the second foot 32 according to the above first magnitude of adjustment H2 to allow the second point to be calibrated 42 to be located on the first reference plane 21. In one embodiment, a lifting operation may be performed on the second foot 32 directly according to the first magnitude of adjustment H2 to adjust the second foot 32 so as to allow the second foot 32 to be consistent with the height of the first foot 31.

By performing the above steps, when all the points to be calibrated on the working plane 21 are located on the first reference plane (heights of all feet are consistent with each other), the working plane 21 can be allowed to be overlapped with the first reference plane to achieve the aim of calibrating a plane (e.g., being in parallel with the horizontal plane).

Optionally, the adjusting step S15 may include the following step: adjusting the second foot 32 to allow a variation value of its height to be equal to the first amplitude of adjustment H2. For example, in one embodiment, the second foot 32 may be stretched (or heightened) or shrunk (or reduced) directly to increase or decrease the height (or altitude) of the second foot 32 by the first amplitude of adjustment H2.

Optionally, in another embodiment, when a knob operation or other specific operations need to be performed on the second foot 32 so as to change its height or altitude, the adjusting step S15 may include a first calibration parameter obtaining step and a step for performing operation on the second foot 32 according to the first calibration parameter, specifically as follows:

dividing the first amplitude of adjustment by a height for a single operation on the second foot 32 to obtain the first calibration parameter; and performing a height adjusting operation on the second foot 32 with the first calibration parameter.

The above first calibration parameter includes operation times of the height adjusting operation performed on the second foot 32, and the height for the single operation on the second foot 32 is a variation value of the height of the second foot 32 after one height adjusting operation has been performed on the second foot 32.

For example, if one clockwise rotation operation is performed on the second foot 32 and its height is decreased by a, then the obtained first amplitude of adjustment H2 is divided by a, and the first calibration parameter can be obtained, which may be a natural number, e.g., N. Then after N times of clockwise rotation have been performed on the second foot 32, the height of the second foot 32 may be decreased by a*N (i.e., the first amplitude of adjustment H2) to be equal to the height of the first foot 31.

As shown in FIG. 2, for the third point to be calibrated 43, if no inclination angle at which the working plane 21 is measured along a direction of a line connecting the third point to be calibrated 43 and the first point to be calibrated 41 (i.e., the above diagonal) has been pre-stored, the second point to be calibrated 42 or the fourth point to be calibrated 44 that is adjacent to the third point to be calibrated 43 may be used as a second reference point so as to compute a distance h1 between the third point to be calibrated 43 and the second point to be calibrated 42 in the vertical direction or a distance h2 between the third point to be calibrated 43 and the fourth point to be calibrated 44 in the vertical direction and to add the computed distance h1 or h2 to the above vertical distance H2 or subtract the computed distance h1 or h2 from the above vertical distance H2, thereby obtaining a vertical distance H3 between the third point to be calibrated 43 and the first reference plane 23.

Figure 3:
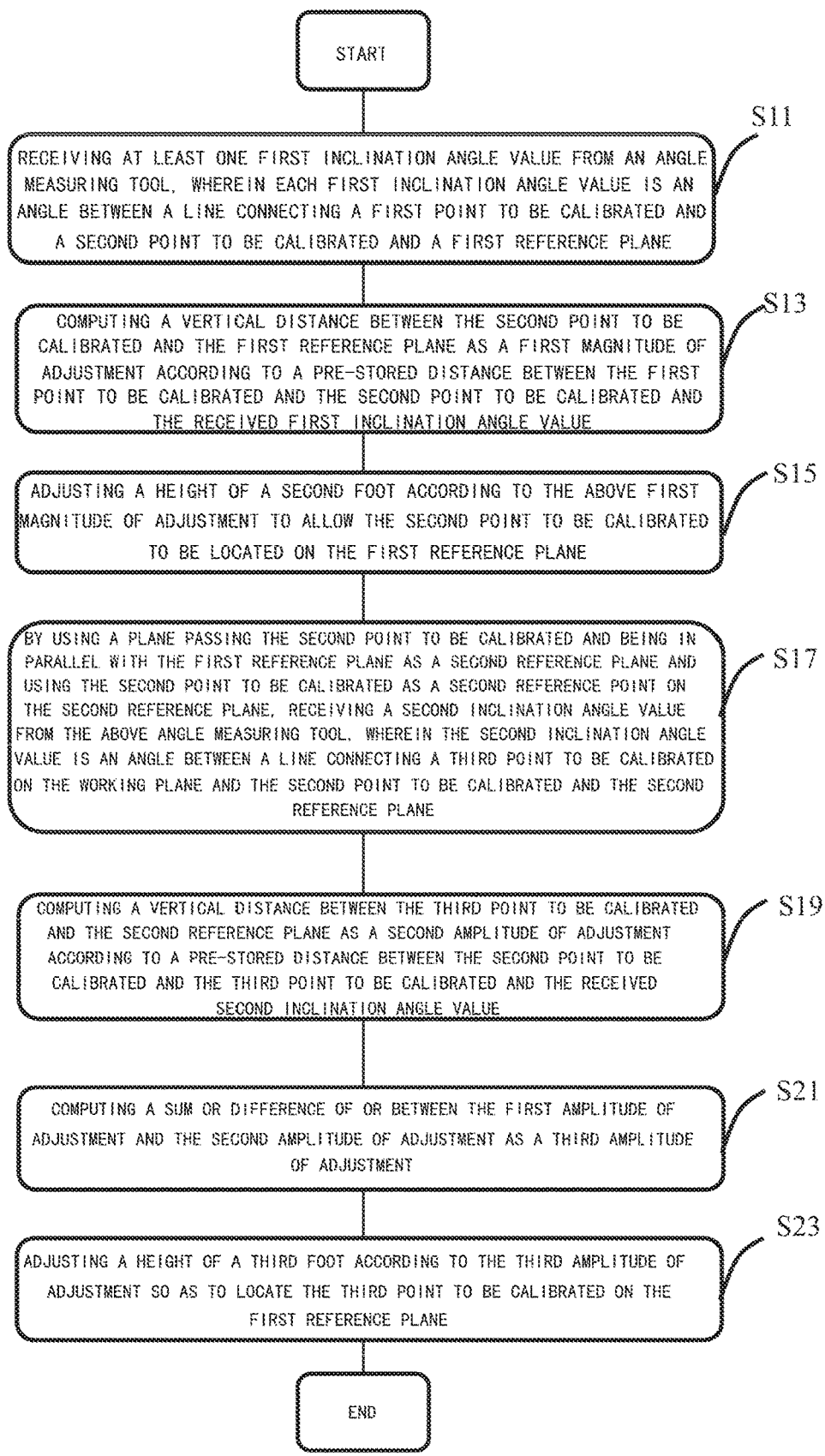
FIG. 3 is a flow chart of a method for calibrating a working plane of a medical detection apparatus provided by another embodiment of the present invention.

FIG. 3 is a flow chart of a method for calibrating a working plane of a medical detection apparatus provided by another embodiment of the present invention. As shown in FIG. 3, take the above third point to be calibrated 43 for illustration, the method for calibrating a working plane of a medical detection apparatus of the present invention may further include the following steps S17, S19, S21 and S23:

Step S17: by using a plane passing the above second point to be calibrated 42 and being in parallel with the first reference plane 23 as a second reference plane 22 and using the second point to be calibrated 42 as a second reference point on the second reference plane 22, receiving a second inclination angle value α2 from the above angle measuring tool, wherein the second inclination angle value α2 is an angle between a line connecting the third point to be calibrated 43 on the working plane 21 and the second point to be calibrated 42 and the second reference plane 22.

Step S19: computing a vertical distance h1 between the third point to be calibrated 43 and the second reference plane 22 as a second amplitude of adjustment according to a pre-stored distance between the second point to be calibrated 42 and the third point to be calibrated 43 and the received second inclination angle value α2.

For example, in Step S19, the above second amplitude of adjustment may be computed by the following Equation (2):

$$h1 = L3 * \tan \alpha 2 \tag{2}$$

Wherein h1 is the above amplitude of adjustment, L3 is a pre-stored distance between the third point to be calibrated 43 and the second point to be calibrated 42, and α2 is the above second inclination angle value.

Step S21: computing a sum or difference of or between the first amplitude of adjustment H2 and the second amplitude of adjustment h1 as a third amplitude of adjustment H3. Those skilled in the art should understand when the third point to be calibrated 43 is higher than the second point to be calibrated 42, a sum of the first amplitude of adjustment H2 and the second amplitude of adjustment h1 is computed as the third amplitude of adjustment H3; otherwise, when the third point to be calibrated 43 is lower than the second point to be calibrated 42, a difference between the first amplitude of adjustment H2 and the second amplitude of adjustment h1 is computed as the third amplitude of adjustment H3.

Step S23: adjusting the height of the third foot 33 according to the third amplitude of adjustment H3 to allow the third point to be calibrated 43 to be located on the first reference plane 23.

Optionally, Step S23 includes: adjusting the third foot 33 to allow a variation value of its height to be equal to the third amplitude of adjustment H3. For example, the third foot 33 may be stretched (or heightened) or shrunk (or reduced) directly to increase or decrease the height (or altitude) of the third foot 33 by the third amplitude of adjustment H3.

Optionally, when knob or other specific operations need to be performed on the third foot 33 to change its height or altitude, Step S23 may include the following steps:

dividing the third amplitude of adjustment H3 by a height for a single operation on the third foot 33 to obtain a second calibration parameter; and performing a height adjusting operation on the third foot 33 with the second calibration parameter.

The above second calibration parameter includes operation times of the height adjusting operation performed on the third foot 33, and the height for the single operation on the third foot 33 is a variation value of the height of the third foot 33 after a single height adjusting operation has been performed on the third foot 33.

In an embodiment of the present invention, the above angle measuring tool may be a digital angle measuring instrument and be configured to output a signal to the medical detection apparatus.

In an embodiment of the present invention, a vertical distance between a point to be calibrated and a reference plane is computed by receiving an inclination angle value of a working plane in a particular direction (e.g., a direction of a line connecting the point to be calibrated and a reference point) with respect to the reference plane from an angle measuring tool and according to a pre-stored distance between the point to be calibrated and the reference point (e.g., between the second point to be calibrated 42 and the first point to be calibrated 41, between the fourth point to be calibrated 44 and the first point to be calibrated 41, between the third point to be calibrated 43 and the second point to be calibrated 42, between the third point to be calibrated 43 and the fourth point to be calibrated 44) and the received inclination angle value, as an amplitude of adjustment at the point to be calibrated, such that a height of a foot at the point to be calibrated can be adjusted quickly and precisely to allow the working plane to be parallel with the reference plane, avoiding repeatedly performing a foot adjusting operation only according to observation of naked eyes and individual experience, greatly improving efficiency of calibrating the working plane.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the Claims.

What is claimed is:

1. A method for calibrating a working plane of a medical detection apparatus, which is used for calibrating said working plane of said medical detection apparatus to be parallel with a first reference plane, wherein said working plane has a first point to be calibrated and a second point to be calibrated thereon, said first point to be calibrated serving as a first reference point and located on said first reference plane, and said first point to be calibrated and said second point to be calibrated are respectively supporting points of a first foot and a second foot on said working plane on said medical detection apparatus, the first foot and the second foot for supporting said working plane, said method for calibrating a working plane of a medical detection apparatus comprising:

receiving at least one first inclination angle value from an angle measuring tool, wherein each first inclination angle value is an angle between a line connecting said first point to be calibrated and said second point to be calibrated and said first reference plane;

computing a vertical distance between said second point to be calibrated and said first reference plane as a first amplitude of adjustment according to a pre-stored distance between said first point to be calibrated and said second point to be calibrated and the received first inclination angle value; and adjusting a height of said second foot according to said first amplitude of adjustment to allow said second point to be calibrated to be located on said first reference plane.

2. The method for calibrating a working plane of a medical detection apparatus according to claim 1, wherein said method for calibrating a working plane of a medical detection apparatus computes said first amplitude of adjustment according to the following equation:

$$H2 = L2 * \tan \alpha 1$$

wherein H2 is said first amplitude of adjustment, L2 is said pre-stored distance between said first point to be calibrated and said second point to be calibrated, and α1 is said first inclination angle value.

3. The method for calibrating a working plane of a medical detection apparatus according to claim 1, wherein said "adjusting a height of said second foot according to said first amplitude of adjustment to allow said second point to be calibrated to be located on said first reference plane" comprises:

adjusting said second foot to allow a variation value of its height to be equal to said first amplitude of adjustment.

4. The method for calibrating a working plane of a medical detection apparatus according to claim 1, wherein said "adjusting a height of said second foot according to said first amplitude of adjustment to allow said second point to be calibrated to be located on said first reference plane" comprises:

dividing said first amplitude of adjustment by a height for a single operation on said second foot to obtain a first calibration parameter, wherein said first calibration parameter comprises operation times for a height adjusting operation performed on said second foot, and said height for a single operation on said second foot is a variation value of a height of said second foot after one height adjusting operation has been performed on said second foot; and performing a height adjusting operation on said second foot with said first calibration parameter.

5. The method for calibrating a working plane of a medical detection apparatus according to claim 1, further comprising the following steps:

by using a plane passing said second point to be calibrated and being in parallel with said first reference plane as a second reference plane and using said second point to be calibrated as a second reference point on said second reference plane, receiving a second inclination angle value from said angle measuring tool, wherein said second inclination angle value is an angle between a line connecting one third point to be calibrated on said working plane and said second point to be calibrated and said second reference plane, wherein said third point to be calibrated is a supporting point of a third foot on said working plane on said medical detection apparatus, the third foot for supporting said working plane;

computing a vertical distance between said third point to be calibrated and said second point to be calibrated as a second amplitude of adjustment according to a pre-stored distance between said second point to be calibrated and said third point to be calibrated and the received second inclination angle value;

computing a sum or difference of or between said first amplitude of adjustment and said second amplitude of adjustment as a third amplitude of adjustment; and adjusting a height of said third foot according to said third amplitude of adjustment to allow said third point to be calibrated to be located on said first reference plane.

6. The method for calibrating a working plane of a medical detection apparatus according to claim 5, wherein said "adjusting a height of said third foot according to said third amplitude of adjustment to allow said third point to be calibrated to be located on said first reference plane" comprises:

adjusting said third foot to allow a variation value of its height to be equal to said third amplitude of adjustment.

7. The method for calibrating a working plane of a medical detection apparatus according to claim 5, wherein said "adjusting a height of said third foot according to said third amplitude of adjustment to allow said third point to be calibrated to be located on said first reference plane" comprises:

dividing said third amplitude of adjustment by a height for a single operation on said third foot to obtain a second calibration parameter, wherein said second calibration parameter comprises operation times of a height adjusting operation performed on said third foot, and said height for a single operation on said third foot is a variation value of a height of said third foot after one height adjusting operation has been performed on said third foot; and performing a height adjusting operation on said third foot with said second calibration parameter.

8. The method for calibrating a working plane of a medical detection apparatus according to claim 5, wherein said method for calibrating a working plane of a medical detection apparatus computes said second amplitude of adjustment according to the following equation:

$$H2 = L3 * \tan \alpha 2$$

wherein H2 is said second amplitude of adjustment, L3 is said pre-stored distance between said third point to be calibrated and said second point to be calibrated, and α2 is said second inclination angle value.

9. The method for calibrating a working plane of a medical detection apparatus according to claim 1, wherein said angle measuring tool is a digital angle measuring instrument and configured to output a signal to said medical detection apparatus.

\* \* \* \* \*